(12) United States Patent
Koslow (10) Patent No.: US 8,056,733 B2
(45) Date of Patent: *Nov. 15, 2011

(54) STRUCTURES THAT INHIBIT MICROBIAL GROWTH

(75) Inventor: Evan E Koslow, Weston, CT (US)

(73) Assignee: KX Technologies LLC, West Haven, CT (US)

(*) Notice: Subject to any disclaimer, the term of this patent is extended or adjusted under 35 U.S.C. 154(b) by 547 days.

This patent is subject to a terminal disclaimer.

(21) Appl. No.: 11/832,042

(22) Filed: Aug. 1, 2007

(65) Prior Publication Data

US 2007/0298064 A1  Dec. 27, 2007

Related U.S. Application Data

(63) Continuation of application No. 10/640,889, filed on Aug. 14, 2003, now Pat. No. 7,287,650, which is a continuation-in-part of application No. 10/286,695, filed on Nov. 1, 2002, now Pat. No. 6,835,311, and a continuation-in-part of application No. 10/290,803, filed on Aug. 11, 2002, now Pat. No. 6,630,016.

(60) Provisional application No. 60/354,062, filed on Jan. 31, 2002.

(51) Int. Cl.
*B01D 39/00* (2006.01)
*A01N 59/16* (2006.01)
*B01D 61/00* (2006.01)

(52) U.S. Cl. ............... 210/502.1; 210/502; 210/503; 424/78.08; 424/78.17; 424/618; 424/630; 424/638; 424/719

(58) Field of Classification Search .............. None
See application file for complete search history.

(56) References Cited

U.S. PATENT DOCUMENTS

| | | |
|---|---|---|
| 3,716,449 A | 2/1973 | Gatward et al. |
| 4,151,202 A | 4/1979 | Hunter et al. |
| 4,280,925 A | 7/1981 | Kiefer |
| 4,600,620 A | 7/1986 | Lloyd et al. |
| 4,624,890 A | 11/1986 | Lloyd et al. |
| 4,627,953 A | 12/1986 | Johnson |
| 4,643,852 A | 2/1987 | Koslow |
| 4,683,165 A | 7/1987 | Lindemann et al. |
| 4,725,489 A | 2/1988 | Jones et al. |
| 4,728,323 A | 3/1988 | Matson |
| 4,904,524 A | 2/1990 | Yoh |

(Continued)

OTHER PUBLICATIONS

Marsili, R., Techniques for Evaluating Packaging Materials, Food Product Design, http://www.foodproductdesign.com/archive/1997/0297QA.html, printed on Apr. 24, 2003.

*Primary Examiner* — Krishnan S Menon
(74) *Attorney, Agent, or Firm* — DeLio & Peterson, LLC (57) ABSTRACT

Structures treated with a microbiological interception enhancing agent comprising of a water-soluble cationic material having a counter ion associated therewith at specific sites on the cationic material, in combination with a biologically active metal salt, wherein the counter ion associated with the cationic material preferentially precipitates with at least a portion of the cation of the biologically active metal salt such that precipitation of the biologically active metal cation and the counter ion associated with the cationic material occurs in proximity to the cationic material are disclosed herein. The microbiological interception enhancing agent may be incorporated into articles of commerce by treating the starting materials of the structure or by applying the microbiological interception enhancing agent on to at least one surface of the article.

22 Claims, 2 Drawing Sheets

U.S. PATENT DOCUMENTS

| | | |
|---|---|---|
| 4,929,502 A | 5/1990 | Giglia |
| 4,986,882 A | 1/1991 | Mackey et al. |
| 5,131,590 A | 7/1992 | Sperber |
| 5,147,338 A | 9/1992 | Lang et al. |
| 5,164,045 A | 11/1992 | Awofeso et al. |
| 5,185,411 A | 2/1993 | Jueptner et al. |
| 5,203,764 A | 4/1993 | Libbey et al. |
| 5,213,884 A | 5/1993 | Fellows |
| 5,457,136 A | 10/1995 | Hartranft et al. |
| 5,503,908 A | 4/1996 | Faass |
| 5,681,468 A | 10/1997 | Sawan |
| 5,720,851 A | 2/1998 | Reiner |
| 5,849,311 A | 12/1998 | Sawan |
| 5,900,258 A | 5/1999 | Engler |
| 6,034,010 A | 3/2000 | Cartwright et al. |
| 6,180,584 B1 | 1/2001 | Sawan et al. |
| 6,282,680 B1 | 8/2001 | Takagi et al. |
| 6,340,663 B1 | 1/2002 | Deleo et al. |
| 6,387,415 B1 | 5/2002 | Garris |
| 6,413,368 B1 | 7/2002 | Dwiggins et al. |
| 6,426,382 B1 | 7/2002 | Farrar et al. |
| 6,440,405 B1 | 8/2002 | Cooper et al. |
| 6,500,302 B2 | 12/2002 | Dwiggins et al. |
| 6,518,479 B1 | 2/2003 | Graef et al. |
| 6,525,240 B1 | 2/2003 | Graef et al. |
| 6,531,078 B2 | 3/2003 | Laine et al. |
| 6,579,906 B2 | 6/2003 | Cooper et al. |
| 6,589,665 B2 | 7/2003 | Chabrecek et al. |
| 6,630,016 B2 | 10/2003 | Koslow |
| 6,835,311 B2 | 12/2004 | Koslow |
| 6,913,154 B2 | 7/2005 | Koslow |
| 6,953,604 B2 | 10/2005 | Koslow |
| 6,959,820 B2 | 11/2005 | Koslow |
| 6,988,058 B1 | 1/2006 | Sherwin et al. |
| 7,008,537 B2 | 3/2006 | Koslow |
| 2002/0022012 A1 | 2/2002 | Cooper et al. |
| 2002/0089079 A1 | 7/2002 | Shelley et al. |
| 2002/0090499 A1 | 7/2002 | Shelley et al. |
| 2002/0094423 A1 | 7/2002 | Stepanian et al. |
| 2003/0082133 A1 | 5/2003 | Cooper et al. |

STRUCTURES THAT INHIBIT MICROBIAL GROWTH

This application is a continuation of U.S. patent application Ser. No. 10/640889, filed Aug. 14, 2003, now U.S. Pat. No. 7,287,650, which is a continuation-in-part of (1) U.S. patent application Ser. No. 10/286,695 filed on Nov. 1, 2002, now U.S. Pat. 6,835,311; and (2) U.S. patent application Ser. No. 10/290,803, filed Aug. 11, 2002, now U.S. Pat. No. 6,630,016. Both 10/286,695 and 10/290,803 claim priority over the U.S. Provisional Patent Application 60/354,062 filed Jan. 31, 2002.

The present invention is directed to structures and compositions that inhibit microbial growth on surfaces that are contacted with such structures, and methods of making and using same.

SUMMARY OF THE INVENTION

The present invention is directed to an anti-microbial structure comprising of: a microbiological interception enhancing agent comprising of a water-soluble cationic material having a counter ion associated therewith, in combination with a biologically active metal salt, wherein the counter ion associated with the cationic material preferentially precipitates with at least a portion of the biologically active metal cation such that precipitation of the biologically active metal cation and the counter ion occurs in proximity to the cationic material.

In another aspect, the present invention is directed to an anti-microbial structure comprising of: a microbiological interception enhancing agent comprising a homopolymer of diallyl dimethyl ammonium halide wherein the halide is a counter ion of the ammonium cation, in combination with a silver salt, wherein the halide counter ion preferentially precipitates with at least a portion of the silver cation such that precipitation of the silver cation and the halide counter ion occurs in proximity to the homopolymer of diallyl dimethyl ammonium halide.

The anti-microbial structures of the present invention may further include a plurality of nanofibers wherein the plurality of nanofibers is coated with or contains the microbiological interception enhancing agent. The plurality of nanofibers treated with the microbiological interception enhancing agent can be formed into a high-loft cellular foam or other fibrous structures, including membranes, woven and nonwoven materials, textiles, wound dressings, sponges, and the like. Non-fibrous structures treated with the microbiological interception enhancing agent can be made into films, extruded, molded, or cast structures from metal, glass, wood, polymers, or composites thereof.

The microbiological interception enhancing agent can also be one of spray coated, painted, dipped, crosslinked, adsorbed, and absorbed on at least one surface of the anti-microbial structure. The microbiological interception enhancing agent can also be incorporated or compounded with the starting materials of the anti-microbial structure. In polymer processing, the microbiological interception enhancing agent can be compounded with the polymeric resin or combined with other polymer processing additives.

In yet another aspect, the present invention is directed to a process of making an anti-microbial structure comprising of: treating at least a portion of an article with a microbiological interception enhancing agent comprising of a water-soluble cationic material having a counter ion associated therewith, in combination with a biologically active metal salt, wherein the counter ion associated with the cationic material preferentially precipitates with at least a portion of the biologically active metal cation such that precipitation of the biologically active metal cation and the counter ion occurs in proximity to the cationic material.

Preferably, the step of treating comprises treating at least a portion of the article with a microbiological interception enhancing agent comprising of a homopolymer of diallyl dimethyl ammonium halide wherein the halide is a counter ion of the ammonium cation, in combination with a silver salt, wherein the halide counter ion preferentially precipitates with at least a portion of the silver cation such that precipitation of the silver cation and the halide counter ion occurs in proximity to the homopolymer of diallyl dimethyl ammonium halide.

The step of treating may also comprise of treating at least a portion of a plurality of nanofibers with the microbiological interception enhancing agent, and further including the steps of: adding a binder; forming a foamed dispersion of the plurality of nanofibers and the binder; removing any liquid in the foamed dispersion; and causing the binder to fuse the plurality of nanofibers into a cellular structure.

In yet another aspect, the present invention is directed to a method of inhibiting microbial activity on a structure or article comprising of: treating at least a portion of the structure or article with a water-soluble cationic material having a counter ion associated therewith, in combination with a biologically active metal salt, wherein the counter ion associated with the cationic material preferentially precipitates with at least a portion of the metal cation of the biologically active metal salt such that controlled and direct precipitation of the metal cation and the counter ion occurs in proximity to the cationic material.

BRIEF DESCRIPTION OF THE DRAWINGS

The features of the invention believed to be novel and the elements characteristic of the invention are set forth with particularity in the appended claims. The figures are for illustration purposes only and are not drawn to scale. The invention itself, however, both as to organization and method of operation, may best be understood by reference to the description of the preferred embodiment(s) that follows taken in conjunction with the accompanying drawings in which:

DETAILED DESCRIPTION OF THE PREFERRED EMBODIMENT(S)

Structures of the present invention are treated with a microbiological interception enhancing agent that inhibits microbial growth making the structures useful in medical devices such as surgical drapes, wound dressings, liners, and transcutaneous products; packaging materials, particularly in the food industry to deter spoilage; cleaning products such as wipes and sponges; disposable clean suits; fibers; and plastic components. In some cases, the structures of the present invention have high surface areas and strong capillary action to intercept microbiological contaminants on surfaces contacted with the structures of the present invention. The microbiological interception enhancing agent may be incorporated into articles of commerce by treating the starting materials of the structure or by applying the microbiological interception enhancing agent on to at least one surface of the article.

The Microbiological Interception Enhancing Agent

The microbiological interception enhancing agent is capable of creating a positive charge on at least a portion of the surface of the structures of the present invention. The chemical treatment produces a strong positive charge upon the treated surfaces as measured using streaming or zeta potential analysis and this positive charge is retained at pH values below 10. The cationic material may be a colloid, a small charged molecule or a linear or branched polymer having positively charged atoms along the length of the polymer chain. The cationic material has a counter ion associated therewith. Preferably, the cationic material is water soluble and readily ionizes in an aqueous medium, but has the capacity to be bonded, adsorbed, or incorporated into the surface or bulk of the structure. The cationic material is present on at least a portion of the surface of the structure. The microbiological interception enhancing agent further includes a biologically active metal in direct proximity to the cationic material.

If the cationic material is a polymer, the charge density is preferably greater than about 1 charged atom per about every 30 Angstroms, preferably greater than about 1 charged atom per about every 20 Angstroms, and more preferably greater than about 1 charged atom per about every 10 Angstroms of molecular length. The higher the charge density on the cationic material, the higher the concentration of the counter ion associated therewith. A high concentration of an appropriate counter ion can be used to drive the precipitation of the biologically active metal. The high charge density of the cationic material provides the ability to adsorb and significantly reverse the normal negative charge of the structure material, making it more useful for microbiological interception. The cationic material should consistently provide a highly positively charged surface to the structure as determined by a streaming or zeta potential analyzer, whether in a high or low pH environment.

The cationic material can have a molecular weight greater than or equal to about 5000 Daltons, preferably greater than or equal to 100,000 Dalton, more preferably greater than or equal to about 400,000 Daltons, and can be greater than or equal to about 5,000,000 Daltons. The cationic material includes, but is not limited to, quaternized amines, quaternized amides, quaternary ammonium salts, quaternized imides, benzalkonium compounds, biguanides, cationic aminosilicon compounds, cationic cellulose derivatives, cationic starches, quaternized polyglycol amine condensates, quaternized collagen polypeptides, cationic chitin derivatives, cationic guar gum, colloids such as cationic melamine-formaldehyde acid colloids, inorganic treated silica colloids, polyamide-epichlorohydrin resin, cationic acrylamides, polymers and copolymers thereof, combinations thereof, and the like. Charged molecules useful for this application can be small molecules with a single charged unit and capable of being attached to at least a portion of the structure. The cationic material preferably has one or more counter ions associated -therewith which, when exposed to a biologically active metal salt solution in an aqueous medium, cause preferential precipitation of a colloidal metal precipitate in direct proximity to the cationic material. The counter ion associated with the cationic material preferentially precipitates with at least a portion of the cation of the biologically active metal salt such that controlled and direct precipitation of a colloidal metal precipitate occurs in proximity to the cationic material. The colloidal metal precipitate, a species comprising of the metal cation and counter ion of the cationic material, is physically trapped within a matrix of the cationic material, or bound to the cationic material either by adsorption, or electrostatic forces.

Exemplary of amines may be pyrroles, epichlorohydrin derived amines, polymers thereof, and the like. Exemplary of amides may be those polyamides disclosed in International Patent Application No. WO 01107090, and the like. Exemplary of quaternary ammonium salts may be homopolymers of diallyl dimethyl ammonium halide, epichlorohydrin derived polyquaternary amine polymers, quaternary ammonium salts derived from diamines and dihalides such as those disclosed in U.S. Pat. Nos. 2,261,002, 2,271,378, 2,388,614, and 2,454,547, all of which are incorporated by reference, and in International Patent Application No. WO 97/23594, also incorporated by reference, polyhexamethylenedimethylammonium bromide, and the like. The cationic material may be chemically bonded, adsorbed, or crosslinked to a fibrous starting material, to an active particle or fiber captured within the fibrous material, to at least a portion of the surface of, or incorporated into a non-fibrous structure.

Furthermore, other materials suitable for use as the cationic material include BIOSHIELD® available from BioShield Technologies, Inc., Norcross, Ga. BIOSHIELD® is an organosilane product including approximately 5% by weight octadecylaminodimethyltrimethoxysilylpropyl ammonium chloride and less than 3% chloropropyltrimethoxysilane. Another material that may be used is SURFACINE®, available from Surfacine Development Company LLC, Tyngsboro, Mass. SURFACINE® comprises a three-dimensional polymeric network obtained by reacting poly(hexamethylenebiguanide) (PHMB) with 4,4'-methlyene-bis-N,N-dilycidylaniline (MBGDA), a crosslinking agent, to covalently bond the PHMB to a polymeric surface. Silver, in the form of silver iodide, is introduced into the network, and is trapped as submicron-sized particles. The combination is an effective biocide, which may be used in the present invention.

The cationic material when exposed to an aqueous biologically active metal salt solution forms the colloidal metal precipitate that precipitates on at least a portion of the surface of the treated structure. For this purpose, the metals that are biologically active are preferred. Such biologically active metals include, but are not limited to, silver, copper, zinc, cadmium, mercury, antimony, gold, aluminum, platinum, palladium, and combinations thereof. The most preferred biologically active metals are silver and copper. The biologically active metal salt solution is preferably selected such that the metal and the counter ion of the cationic material are substantially insoluble in an aqueous environment to drive precipitation of the colloidal metal precipitate. Preferably, the metal is present in an amount of about 0.01% to about 2.0% by weight of the structure.

A particularly useful microbiological interception enhancing agent is a silver-amine-halide complex. The cationic material is preferably a homopolymer of diallyl dimethyl ammonium halide having a molecular weight of about 400,000 Daltons or other quaternary ammonium salts having a similar charge density and molecular weight. A homopolymer of diallyl dimethyl ammonium chloride useful in the present invention is commercially available from Nalco Chemical Company of Naperville, Ill., under the tradename MERQUAT® 100. The chloride counter ion may be replaced with a bromide or iodide counter ion. When contacted with a silver nitrate solution, the silver-amine-halide complex precipitates on at least a portion of the surface or structure so treated.

Nanofiber-Based Structures

One preferred embodiment of the present invention comprises wovens, nonwovens, membranes, webs, or high loft structures made using wet laid or dry laid processes from a plurality of fibers treated with the microbiological interception enhancing agent. Structures of the present invention can be made from a plurality of nanofibers including whiskers or micro-particulate ingredients, of organic and/or inorganic materials including, but not limited to, polymers, ion-exchange resins, engineered resins, ceramics, cellulose, rayon, ramie, wool, cotton, silk, glass, metal, activated alumina, carbon or activated carbon, silica, zeolites, diatomaceous earth, activated bauxite, fuller's earth, calcium hydroxyappatite, other adsorbent materials, or combinations thereof. Combinations of organic and inorganic fibers and/or whiskers or micro-particulates are contemplated and within the scope of the invention as for example, glass, ceramic, or metal fibers and polymeric fibers may be used together with very small particles incorporated into the final structure.

When produced by a wet laid process from fibers such as cellulose or polymer nanofibers, such nanofibers should have a Canadian Standard Freeness of less than or equal to about 100, and most preferably less than or equal to about 45. Preferably, a significant portion of the nanofibers should have a diameter less than or equal to about 1000 nanometers, more preferably less than or equal to about 400 nanometers, and nanofibers less than or equal to about 250 nanometers in diameter are most preferred. It is preferable to chop the nanofibers to a length of about 1 millimeter to about 8 millimeters, preferably about 2 millimeters to about 6 millimeters, and more preferably about 3 millimeters to about 4 millimeters. Fibrillated nanofibers are most preferred due to their exceptionally fine dimensions and potentially low cost.

Preferably, fibrillated synthetic cellulose nanofibers, processed in accordance with the present invention, can be used to produce an ultra-fine, hydrophilic structure. Such cellulose fibers can be made by direct dissolution and spinning of wood pulp in an organic solvent, such as an amine oxide, and are known as lyocell fibers. Lyocell fibers have the advantage of being produced in a consistent, uniform manner, thus yielding reproducible results, which may not be the case for, for example, natural cellulose fibers. Further, the fibrils of lyocell can be produced by careful exposure to high-shear fields and are often curled. The curls provide a significant amount of fiber entanglement, resulting in a finished sheet with high dry strength and significant residual wet strength. Furthermore, the fibrillated lyocell nanofibers may be produced in large quantities using equipment of modest capital cost. It will be understood that fibers other than cellulose may be fibrillated to produce extremely fine fibrils, such as for example, artificial fibers, in particular, acrylic or nylon fibers, or other natural cellulosic materials. Combinations of fibrillated and non-fibrillated nanofibers may be used.

Dry laid processes of making the nanofiber-based structures include spun bonding, electrospinning, islands-in-sea processes, fibrillated films, melt blowing, and other processes known to one of skill in the art. An exemplary dry laid process starts with staple fibers, which can be separated by carding into individual fibers and are then laid together to a desired thickness by an aerodynamic or hydrodynamic process to form an unbonded fiber sheet. The unbonded fibers can then be subjected to hydraulic jets to both fibrillate and hydroentangle the fibers. A similar process can be performed on certain plastic films that when exposed to high pressure jets of water, are converted into webs of fibrillated fibers.

Membranes

Fibrous membrane structures can also be made in accordance with processes known to one of skill in the art. Nanofibers for the membrane may be treated with the microbiological interception enhancing agent prior to forming the membrane. The microbiological interception enhancing agent can also be applied to the finished membrane using known methods in the art similar to those used to treat the fibers. Calendaring the membranes can also yield membranes of desired permeability. Membranes of organic or inorganic composition include, but are not limited to, polymers, ion-exchange resins, engineered resins, ceramics, cellulose, rayon, ramie, wool, silk, glass, metal, activated alumina, activated carbon, silica, zeolites, diatomaceous earth, activated bauxite, fuller's earth, calcium hydroxyappatite, titanates and other materials, or combinations thereof. Combinations of organic and inorganic materials are contemplated and within the scope of the invention. Microparticulates can be imbedded into the membrane to provide additional functionality. Resultant membranes can be used in apparel items, vapor barriers, liners, etc.

High-Loft Structures

High loft structures made with nanofibers are formed by dispersing the treated nanofibers in a fluid, and generating a low density foam that is allowed to drain under low suction to prevent collapse of the foam. The foam is created using surfactants, thickeners, and/or binders. Foaming is generated by mechanical agitation, dissolved gas processes, or with chemical foamants. The foam is then cast and dried to produce a high loft fibrous structure. Binders in the nanofiber foam dispersion help maintain the open-cell structure of the foam upon drying. The high loft structures treated with the microbiological interception enhancing agent are useful as sponges, wound dressings, and wipes given their high surface area and strong capillary action.

Figure 1:
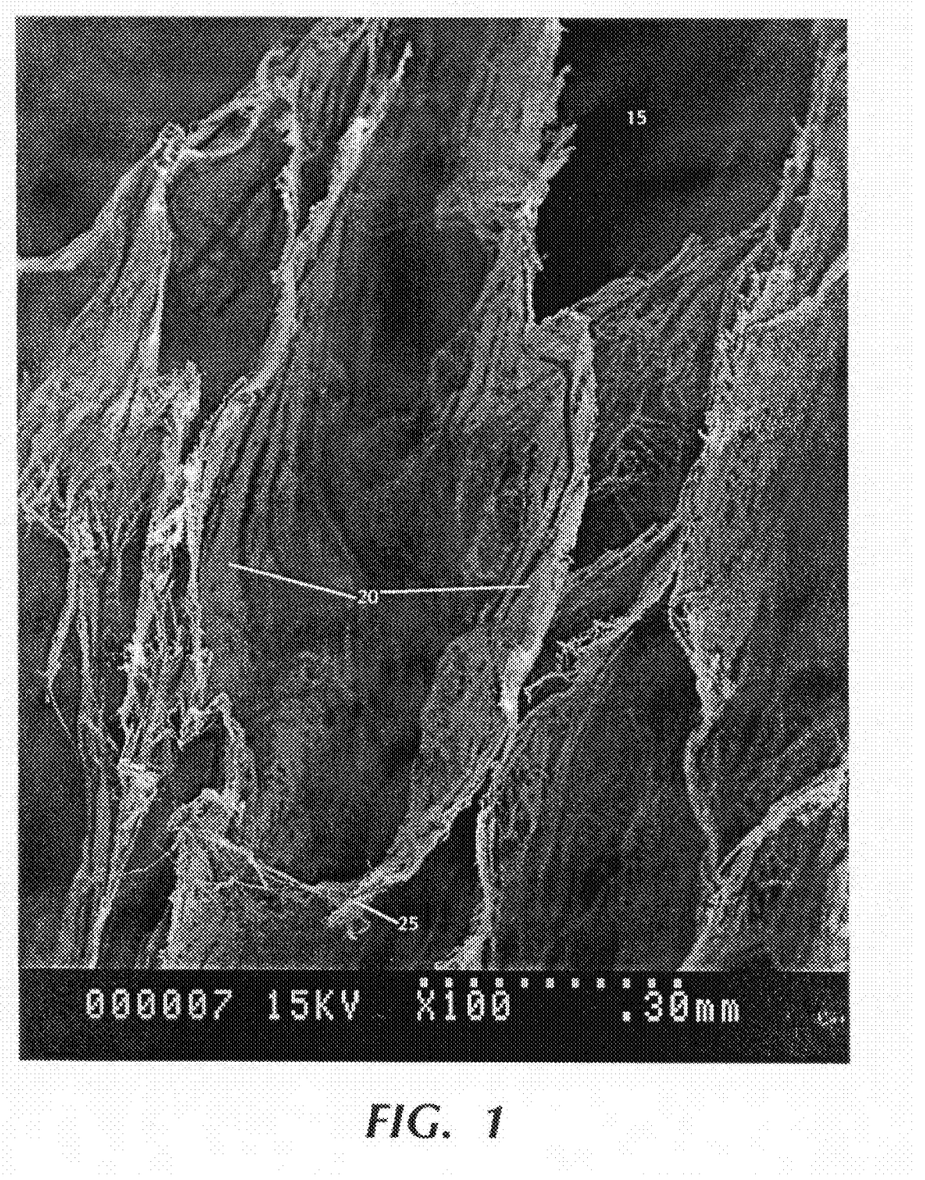
FIG. 1 is a cross sectional view of a structure of the present invention at 100× magnification.
Figure 2:
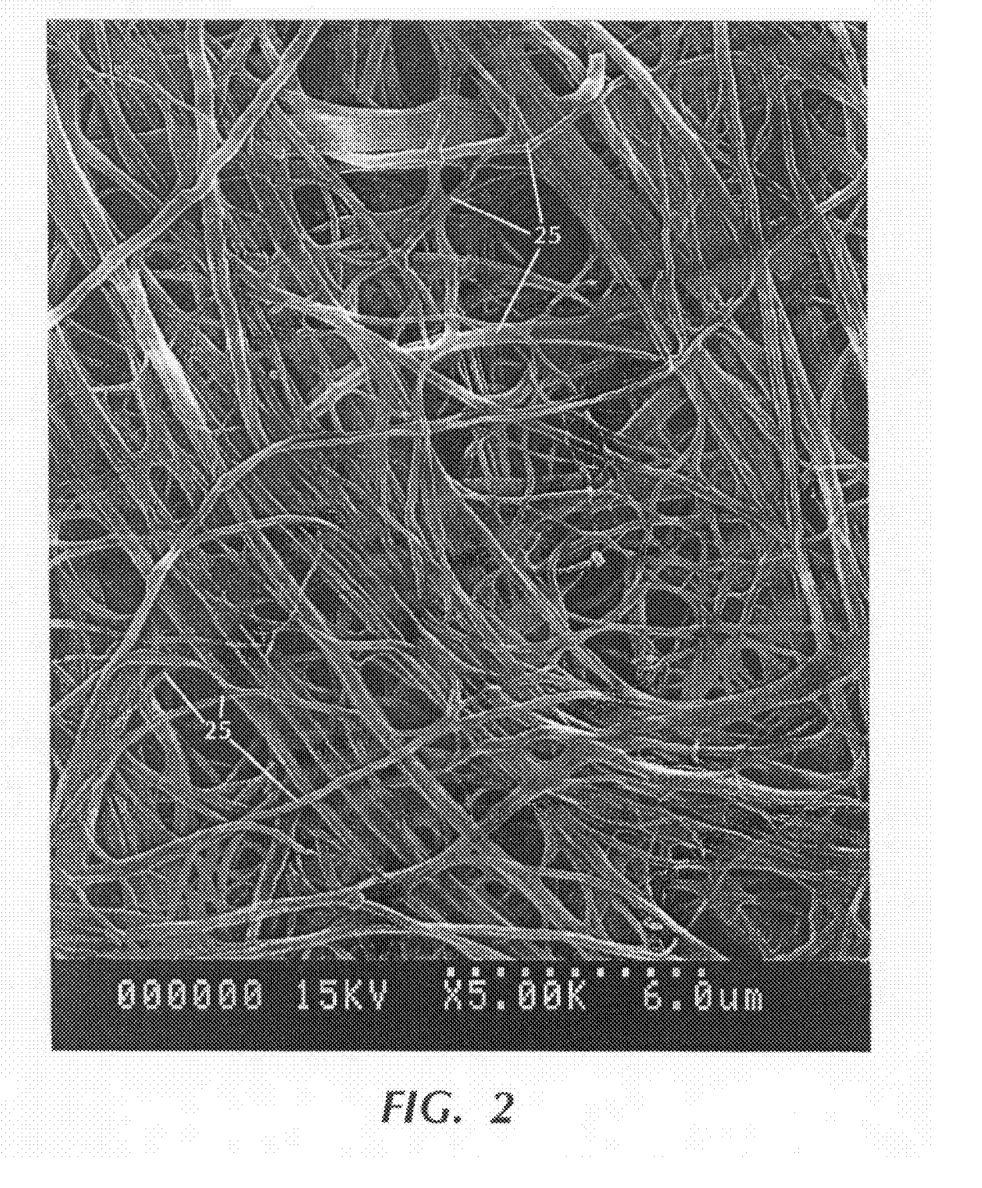
FIG. 2 is a cross sectional view of the structure of FIG. 1 at 5000× magnification.

The high loft structure is a novel structure consisting of nanofibers cast to form a foam that is composed of lenticular cells with porous walls wherein the walls are composed of nanofibers, and having bulk densities of about 0.0005 to about 0.100 g/cm$^3$. Some of these are of exceptional low density and high permeability to serve as high dirt capacity air filters, etc. FIGS. 1 and 2 are scanning electron micrographs of a high loft structure of the present invention. FIG. 1 is a cross sectional view of a high loft structure 10. High loft structure 10 has voids 15 formed by fibrous walls 20. Fibrous walls 20 are made up of a plurality of nanofibers 25. FIG. 2 shows the plurality of nanofibers 25, forming the wall 20 of a single foam cell, at a higher magnification of high loft structure 10.

The high loft structures can be about 1 to about 25 mm in thickness and can achieve HEPA-like particulate interception.

Textile Fibers

Textile fibers may be treated with the microbiological interception enhancing agent prior to being made into yarns that are woven into a fabric. Alternatively, the microbiological interception enhancing agent can be applied to the woven fabric during the finishing process preferably using a wet processing procedure such as, but not limited to, spray coating, dip coating, and/or other processes known in the art. The microbiological interception enhancing agent can provide either a durable finish some of which are surface coatings that have been made insoluble so that they remain on the yarns and fabrics during care, while others are internal finishes that are within the fiber structure. Fabrics having an anti-microbial finish can control the spread of disease and reduce the danger of infection following injury, inhibit unpleasant odors from perspiration and other soil, reduce damage to the fabric from mildew-producing fungi and rot-inducing bacteria. An anti-microbial finish can prevent or inhibit the growth of microorganisms on fabric in a wide variety of apparel, home furnishing, commercial, and industrial products. Apparel items include socks, shoe linings, foundation garments, sportswear, children's clothing, and diapers. Sheets, pillowcases, mattress padding and covering, surgical drapes, carpet underpadding, carpeting, blankets, and towels, especially for hospital settings, are other examples of how fabrics with an anti-microbial finish are useful. Fabrics for tents, tarps, and auto covers have a longer life when treated with an anti-microbial finish that reduces damage from rot and mildew.

Additives for Fibrous Structures

The strength of the fibrous structure, especially when wet, may be improved with the addition of various additives. It is well known in the art that the addition of epoxy or acrylic or other resins to the paper making process can provide enhanced wet strength, but these water-dispersed resins and reagents often cause lower permeability to the final product, especially as fiber size becomes very small. Although these resins and resin systems can be used in the current invention, it is also preferable to use thermoplastic or thermoset materials known in the art, and in either powder, particulate or fiber form. It is within the scope of the invention that such thermoplastic or thermoset materials can be treated with the microbiological interception enhancing agent described above.

Useful binder materials include, but are not limited to, polyolefins, polyvinyl halides, polyvinyl esters, polyvinyl alcohols, polyvinyl ethers, polyvinyl sulfates, polyvinyl phosphates, polyvinyl amines, polyamides, polyimides, polyoxidiazoles, polytriazols, polycarbodiimides, polysulfones, polycarbonates, polyethers, polyarylene oxides, polyesters, polyarylates, phenol-formaldehyde resins, melamine-formaldehyde resins, formaldehyde-ureas, ethyl-vinyl acetate copolymers, co-polymers and block interpolymers thereof, and combinations thereof. Variations of the above materials and other useful polymers include the substitution of groups such as hydroxyl, halogen, lower alkyl groups, lower alkoxy groups, monocyclic aryl groups, and the like. Other potentially applicable materials include polymers such as polystyrenes and acrylonitrile-styrene copolymers, styrene-butadiene copolymers, and other non-crystalline or amorphous polymers and structures.

A more detailed list of binder materials that may be useful in the present invention include end-capped polyacetals, such as poly(oxymethylene) or polyformaldehyde, poly(trichloroacetaldehyde), poly(n-valeraldehyde), poly(acetaldehyde), and poly(propionaidehyde); acrylic polymers, such as polyacrylamide, poly(acrylic acid), poly(methacrylic acid), poly(ethyl acrylate), and poly(methyl methacrylate); fluorocarbon polymers, such as poly(tetrafluoroethylene), perfluorinated ethylene-propylene copolymers, ethylene-tetrafluoroethylene copolymers, poly(chlorotrifluoroethylene), ethylene-chlorotrifluoroethylene copolymers, poly(vinylidene fluoride), and poly(vinyl fluoride); polyamides, such as poly(6-aminocaproic acid) or poly(e-caprolactam), poly(hexamethylene adipamide), poly(hexamethylene sebacamide), and poly(11-aminoundecanoic acid); polyaramides, such as poly(imino-1,3-phenyleneiminoisophthaloyl) or poly(m-phenyleneisophthalamide); parylenes, such as poly-2-xylylene, and poly(chloro-1-xylylene); polyaryl ethers, such as poly(oxy-2,6-dimethyl-1,4-phenylene) or poly(p-phenylene oxide); polyaryl sulfones, such as poly(oxy-1,4-phenylene-sulfonyl-1,4-phenyleneoxy-1,4-phenyl-eneisopropylidene-1,4-phenylene), and poly(sulfonyl-1,4-phenylene-oxy-1,4-phenylenesulfonyl4,4'-biphenylene); polycarbonates, such as poly-(bisphenol A) or poly(carbonyidioxy-1,4-phenyleneisopropylidene-1,4-phenylene); polyesters, such as poly(ethylene terephthalate), poly(tetramethylene terephthalate), and poly(cyclohexyl-ene-1,4-dimethylene terephthalate) or poly(oxymethylene-1,4-cyclohexylenemethyleneoxy-terephthaloyl); polyaryl sulfides, such as poly(p-phenylene sulfide) or poly(thio-1,4-phenylene); polyimides, such as poly(pyromellitimido-1,4-phenylene); polyolefins, such as polyethylene, polypropylene, poly(1-butene), poly(2-butene), poly(1-pentene), poly(2-pentene), poly(3-methyl-1-pentene), and poly(4-methyl-1-pentene); vinyl polymers, such as poly(vinyl acetate), poly(vinylidene chloride), and poly(vinyl chloride); diene polymers, such as 1,2-poly-1,3-butadiene, 1,4-poly-1,3-butadiene, polyisoprene, and polychloroprene; polystyrenes; and copolymers of the foregoing, such as acrylonitrilebutadiene-styrene (ABS) copolymers. Polyolefins that may be useful include polyethylene, linear low density polyethylene, polypropylene, poly(1-butene), poly(2-butene), poly(1-pentene), poly(2-pentene), poly(3-methyl-1-pentene), poly(4-methyl-1-pentene), and the like.

A variety of binder fibers, including polyethylene; polypropylene; acrylic; co-polyester bi-component fibers such as polyester-polypropylene, polyester-polyethylene, or polypropylene-polyethylene bi-component fibers; or others, can be used. Certain types of polyethylene fibers, when properly treated, as described below, are optimal, and have the additional benefit of not significantly interfering with the hydrophilic nature of the resulting filter medium when used in modest volumes. Preferred fiber binder materials may include FYBREL® synthetic fibers and/or SHORT STUFF® EST-8, both of which are polyolefin based. FYBREL® is a polyolefin based synthetic pulp that is a highly fibrillated fiber and is commercially available from Mitsui Chemical Company, Japan. FYBREL® has excellent thermal moldability and provides a smooth surface to a finished fiber sheet. SHORT STUFF® EST-8 is commercially available from MiniFibers, Inc., Pittsburgh, Pa., and is a highly fibrillated, high density polyethylene.

Preferably, the binder material is present in an amount of about 1% to about 10% by weight, more preferably about 3% to about 6%, and most preferably about 5%. It is preferable that the binder material have a softening point that is significantly lower than a softening point of the fibers so that the finished fiber sheets can be heated to activate the binder material, while the structure does not melt.

One or more additives either in a particulate, fiber, whisker, or powder form may also be mixed with the fibers or incorporated into the structure to aid in adsorption of other contaminants, participate in the formation of the structure, or add other functionality. Useful additives may include, but are not limited to, metallic particles, activated alumina, activated carbon, silica, polymeric powders and fibers, glass beads or fibers, cellulose fibers, ion-exchange resins, engineered resins, ceramics, zeolites, diatomaceous earth, activated bauxite, fuller's earth, calcium sulfate, other adsorbent materials such as super adsorbent polymers (SAPs), or combinations thereof. The additives can also be chemically treated to impart microbiological interception capabilities depending upon the particular application. The amount of additives is dependent upon the particular use of the resultant structure.

Non-Fibrous Structures

Other structures that can inhibit microbial growth when treated with the microbiological interception enhancing agent include polymeric foams, including polyolefins, SAPs, and other open-cell structures that can be molded into different shapes and densities or formed into composites thereof. Treatment of such porous, absorbent structures with the microbiological interception enhancing agent by spray, dip or submergence coating is simple and economical. Low density polyurethane foam is used in furniture, padding, mattresses, and the like, where inhibition of microbial growth can extend the service life of the product. High density polyurethane foam is useful, for example, as insulation in building construction, appliances, and cars. The inhibition of mold and mildew is highly beneficial in these difficult to reach areas.

Treatment of non-permeable and/or non-absorbent structures, collectively non-permeable structures, such as, for example, sheets; films; foils; closed-cell foams; articles made with metal, wood, glass, polymeric resins; and composites thereof are also useful. An anti-microbial finish by surface treatment of the non-permeable structures with the microbiological interception enhancing agent is effectuated by spray, dip or submergence coating. Depending upon the structure, surface conditioning of the non-permeable structure is required for better adhesion of the microbiological interception enhancing agent. For example, a silane crosslinker or corona treatment can provide enhanced adhesion between the organic microbiological interception enhancing agent and organic or inorganic metal or glass surfaces. Addition of the microbiological interception enhancing agent to starting materials useful in making the non-permeable structures incorporates the agent into the structure without a subsequent coating step. Preferably, the microbiological interception enhancing agent is MERQUAT® 100, a heat stable polyquaternary ammonium salt, in combination with a biologically active metal, can be added to the starting material prior to processing, in-line during processing, or combined with other processing additives. For example, in making polyolefinic films that can inhibit microbial growth, the polyolefin pellets are coated with MERQUAT® 100 and a biologically active metal salt such as silver nitrate prior to film formation. The pellets are then dried and can be directly used in traditional extrusion and molding application without further process adjustments.

Methods of Making Structures That Inhibit Microbial Growth

The structures of the present invention can be made using a number of processes including, but not limited to, weaving individual fibers into fabrics, wet laid processes or dry laid processes such as, but not limited to, paper making processes, wet or dry foam casting, electrospinning, spun bonding, islands-in-sea processes, extrusion or other molding techniques of treated polymers, and the like. Resultant fibrous sheets can be further calendared or stretched to provide high performance membranes of varying density and/or fibrillated films.

In a preferred wet laid process, a fiber tow is chopped to a specific length, usually in the range of about 1 millimeter to about 8 millimeters, and in particular in the range of about 3 millimeters to about 4 millimeters. The chopped fibers are fibrillated in a device having characteristics similar to a blender, or on a large scale, in machines commonly referred to as a "hi-low", a "beater", or a "refiner". The fiber is subjected to repetitive stresses, while further chopping and the reduction of fiber length is minimized. As the fibers undergo these stresses, the fibers split as a result of weaknesses between amorphous and crystalline regions and the Canadian Standard Freeness (CSF), which is determined by a method well known in the art, begins to decline. Samples of the resulting pulp can be removed at intervals, and the CSF used as an indirect measure of the extent of fibrillation. While the CSF value is slightly responsive to fiber length, it is strongly responsive to the degree of fiber fibrillation. Thus, the CSF, which is a measure of how easily water may be removed from the pulp, is a suitable means of monitoring the degree of fiber fibrillation. If the surface area is very high, then very little water will be drained from the pulp in a given amount of time and the CSF value will become progressively lower as the fibers fibrillate more extensively. The fibrillated fiber of a given CSF value can be directly used for producing paper or dewatered on a variety of different devices, including a dewatering press or belt, to produce a dewatered pulp. The dewatered pulp can be subsequently used to make a wet-laid paper.

Generally, for application in the present invention, a pulp with a CSF of below 100 is used, and preferably, the CSF should be less than or equal to about 45.

The pulp is treated with a cationic material in such a manner as to allow the cationic material to coat at least a portion of the surface of at least some of the fibers thereby imparting a charge on the fibers. Methods of applying the cationic material to the fibers are known in the art and include, but are not limited to, spray, dip, or submergence coating to cause adsorption, chemical reaction or crosslinking of the cationic material to the surface of the fibers. The treated pulp is then rinsed in reverse osmosis/deionized (RO/DI) water, partially dewatered, usually under vacuum, to produce a wet lap that can then be exposed to a biologically active metal salt solution. The use of nearly ion-free rinse water causes the counterions associated with the cationic material to be drawn tightly against the treated fiber surface and to eliminate unwanted ions that may cause uncontrolled precipitation of the biologically active metal into sites remote from the cationic surface.

The metal salt solution is infiltrated into the fibers to allow precipitation of the colloidal metal precipitate on a surface of at least a portion of the fibers. The precipitation accurately deposits a colloidal metal precipitate adjacent to the cationic coating because the counter-ion associated with this coating reacts with the applied metal salt to form the colloidal particles. When silver nitrate is used as the metal salt solution, the presence of precipitated silver can be confirmed by using a Kratos EDX-700/800 X-ray fluorescence spectrometer available from Kratos Analytical, a Shimadzu Group Company, Japan. After sufficient exposure to the biologically active metal salt solution, the fibers can be rinsed and excess water is removed. The fibers can be directly sent to pulp preparation systems to create a furnish suitable for paper making.

Exemplary of a wet laid process includes mixing a pulp of 45 CSF fibrillated lyocell nanofibers with 5% EST-8 binder fibers and dispersing the pulp and binder fibers in deionized water with mixing in a blender to form a furnish with about 1% to about 2% consistency. To this mixture is added about 3% by weight of MERQUAT® 100, which is briefly dispersed into the dilute pulp furnish. The cationic material remains in contact with the pulp for about 4 to about 12 hours until a significant portion has been adsorbed onto at least a portion of the nanofibers to impart and maintain a positive zeta potential on the nanofibers. Within about eight hours at room temperature, sufficient MERQUAT® is adsorbed to provide a positive zeta potential on the nanofibers that is greater than about +10 millivolts. Next, this pulp is partially dewatered under vacuum and rinsed with deionized water to form a wet lap. A biologically active metal salt solution, such as, for example, silver nitrate, in an amount equal to 0.5% by weight of the dry nanofibers, is prepared with deionized water, and uniformly poured over the sheet and allowed to stand for a short time to allow precipitation of the biologically active metal with at least a portion of the counter ion associated with the cationic material. Thereafter, the nanofibers can be directly used in the production of fibrous structures that can inhibit microbial growth.

In making a high loft structure, the nanofibers are treated with the microbiological interception enhancing agent and dispersed with a surfactant and/or thickeners to generate and maintain the foamed dispersion. Useful surfactants/thickeners are METHOCEL® made by The Dow Chemical Company, Midland, Mich.; NALCO® PP10-3074 made by Ondeo Nalco, Naperville, Ill.; polyethylene oxide type profoamants, sodium lauryl sulfate, and the like. The foamed nanofibers can be continuously cast using a foraminous wire, and dried to make the high loft structures. Alternatively, the high loft structure can be made and then treated with the microbiological interception enhancing agent using such methods as spray coating, dipping, submergence coating, and the like, such that the microbiological interception enhancing agent is absorbed into the high loft structure.

Exemplary of a dry laid process includes depositing the dried treated fibers on a foraminous wire at high speeds with suction. Other methods include, but are not limited to, electrospinning, spun bonding, and the like. Membranes made from either dry or wet laid processes can be calendared to the desired porosity.

Exemplary of making plastic parts or components that can inhibit microbial growth, includes coating the plastic pellets with MERQUAT® 100 and the biologically active metal salt, such as silver nitrate, prior to forming the plastic part. The pellets are then dried and can be directly used in traditional extrusion and molding applications without further process adjustments.

EXAMPLES

The following examples are provided to illustrate the present invention and should not be construed as limiting the scope of the invention.

Bacterial challenges of the structures were performed using suspensions of *Escherichia coli* of the American Type Culture Collection (ATCC) No. 11775 to evaluate the response to a bacterial challenge. The Standard Operating Procedures of the ATCC were used for propagation of the bacterium, and standard microbiological procedures, as well known in the art, were used for preparing and quantifying the bacteria.

Example 1

Inhibition of Microbial Growth in Fibrous Structures of the Present Invention After Exposure to *E. coli*

Approximately 12 g, dry weight, of lyocell pulp, and 0.45 g of SHORT STUFF® EST-8 polyethylene binder fiber were pre-wetted with hot reverse osmosis/deionized (RO/DI) water. The fibers were blended with 1.8 L of RO/DI water in a Waring blender for about 45 seconds. The fiber mixture was poured into a 30.5×30.5 cm² stainless steel FORMAX® paper deckle filled with about 24.0 L of deionized water and fitted with a 100 mesh forming screen. A 30×30 cm² stainless steel agitator plate having 60 holes of 2 cm in diameter was used to plunge the fiber mixture up and down from top to bottom about 8 to 10 times. The water was removed from the fiber mixture by pulling a slight vacuum below the deckle to cause the fibers to form on the wire. Once the bulk of the water is removed, supplemental dewatering is accomplished with a vacuum pump to remove additional excess moisture and to create a relatively smooth, flat, fairly thin paper-like sheet. The resulting sheet is separated from the screen and combined with a blotter sheet on both top and bottom. The combination of sheets is gently rolled with a 2.27 kg marble rolling pin to remove excess water and smooth out the top surface of the sheet. The sheet is then placed between two fresh and dry blotter sheets and placed on a FORMAX® sheet dryer for about 10 to about 15 minutes at about 120° C. The dried filter medium is separated from the blotter sheets and directly heated on the FORMAX® sheet dryer for about 5 minutes on each side to activate the dry binder fibers.

Discs of 2.0 cm diameter were cut from the lyocell sheet representing the control structures. The control structures were not treated with the microbiological interception enhancing agent and are shown to be incapable of inhibiting microbial growth. Discs treated with the microbiological interception enhancing agent represent structures of the present invention. The discs were treated as follows: each disc received 4 drops of a MERQUAT® 100 solution (3 ml of MERQUAT® 100 in 6 ml of I/DI water), and after drying, the same discs received 2 drops of a silver nitrate solution (1.6 g of $AgNO_3$ in 60 ml I/DI water).

Each disc was placed in intimate contact with *E. coli* cultured overnight by the streaking method on tryptic soy agar (TSA) petri dishes using standard methods. After 1, 4 and 24 hour contact times with the *E. coli* suspension and incubation at 37° C., the discs were removed from each of the petri dishes using a sterile technique, and plated on TSA petri dishes to recover any *E. coli*. Plates were inverted and incubated at 37° C. for 24 hours.

Results are shown in Table 1 below.

TABLE I

|  | Example 1 | Control |
|---|---|---|
| Contact time | 1 hour | 1 hour |
| Colonies (CFU/ml) | TNTC* | TNTC |
| Contact time | 4 hours | 4 hours |
| Colonies (CFU/ml) | $4.0 \times 10^6$ | TNTC |
| Contact time | 24 hours | 24 hours |
| Colonies (CFU/ml) | 0 | TNTC |

*TNTC = Too numerous to count.

After exposing the structures of the present invention to microbiological contaminants, the microbiological interception enhancing agent renders the structure of the present invention substantially free of contaminants for subsequent use.

Example 2

Inhibition of Microbial Growth in Plastic Structures of the Present Invention After Exposure To *E. coli*

The anti-microbial activity of treated polypropylene components were compared with untreated polypropylene components (Control). Polypropylene beads of about 3-4 millimeters (1198 g) were coated with 32.5 ml MERQUAT® 100 with gentle mixing. A solution of silver nitrate, 4.55 g in 20 ml RO/DI water, was sprayed onto the MERQUAT® 100 coated beads. Mixing took place for about 5 minutes and the beads dried with a heat gun for about 15 minutes. The treated beads were injection molded into filter endcaps according to conditions known to one skilled in the art.

An *E. coli* suspension was prepared overnight using the streaking method on a TSA plate to obtain isolated colonies. A single isolated colony was used to prepare an *E. coli* dilution. A portion of the *E. coli* dilution, 0.01 ml, was cultured on TSA, and the spread method was used to cover the entire agar plate. A portion of the treated filter endcap was placed on the cultured plate and incubated overnight at 37° C. An untreated filter endcap was placed on another cultured plate to serve as the Control.

After 18 hours on the cultured plate, there was a visible inhibition zone around and beneath the treated endcap indicating the anti-microbial effect of the polypropylene treated with the microbiological interception enhancing agent. After 18 hours, the Control shows no such inhibition zone, and beneath the endcap there are visible colonies of bacterial growth.

The treated structures of the present invention are useful as packaging papers, liners, disposable products, wipes, sponges, and other like products where inhibition of microbial growth is desirable. The microbiological interception enhancing agent inhibits the further growth of microbiological contaminants retained in or on the structure after contact with a contaminated surface.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

What is claimed is:

1. A process of making an anti-microbial structure comprising:
   providing a dry base structure comprising starting materials for use in fabricating a dry article;
   providing a microbiological interception enhancing agent comprising a cationic material having one or more counter ions associated therewith and a biologically active metal salt;
   treating at least a portion of a surface of said starting materials with said cationic material;
   exposing said treated starting materials to said biologically active metal salt, whereby said one or more counter ions of said cationic material preferentially precipitate with at least a portion of said biologically active metal salt such that precipitation of a colloidal metal precipitate occurs in direct proximity to said cationic material, while avoiding uncontrolled precipitation of said biologically active metal salt at sites of said starting materials remote from said cationic material, such that, said microbiological interception enhancing agent resides on said at least portion of said surface of said starting materials; and fabricating said dry article using said starting materials having said microbiological interception enhancing agent whereby both said starting materials and said microbiological interception enhancing agent reside throughout the finished dry article.

2. The process of claim 1 wherein said starting materials and said microbiological interception enhancing agent reside throughout the entire thickness of said article.

3. The process of claim 1 wherein said starting materials of said dry base structure are selected from the group consisting of nanofiber-based structures, membranes, high-loft structures, textile fibers, non-fibrous structures, non-permeable structures and non-absorbent structures.

4. The process of claim 3 wherein said nanofiber-based structures comprise a plurality of nanofibers treated with said microbiological interception enhancing agent.

5. The process of claim 4 wherein said plurality of nanofibers comprise a plurality of activated fibrillated nanofibers.

6. The process of claim 4 wherein the step of treating comprises treating at least a portion of a surface of at least some of said nanofibers with said cationic material.

7. The process of claim 4 further including the steps of:
   adding a binder;
   forming a foamed dispersion of the plurality of nanofibers and the binder;
   removing any liquid in the foamed dispersion; and
   causing the binder to fuse the plurality of nanofibers into a cellular structure.

8. The process of claim 4 wherein said plurality of nanofibers treated with said microbiological interception enhancing agent comprise dry materials selected from the group consisting of polymers, ion-exchange resins, engineered resins, ceramics, cellulose, rayon, ramie, wool, silk, glass, metal, activated alumina, activated carbon, silica, zeolites, diatomaceous earth, activated bauxite, fuller's earth, calcium hydroxyappatite and combinations thereof.

9. The process of claim 3 wherein said nanofiber-based structures treated with said microbiological interception enhancing agent are used in the fabrication of dry articles selected from the group consisting of wovens, non-wovens, membranes, webs, high-loft structures, whiskers and microparticulates made using wet laid or dry laid processes.

10. The process of claim 3 wherein said textile fibers treated with said microbiological interception enhancing agent include woven fabrics used in the fabrication of dry articles selected from the group consisting of socks, shoe linings, foundation garments, sportswear, children's clothing, diapers, sheets, pillowcases, mattress padding, mattress covering, surgical drapes, carpet underpadding, carpeting, blankets, towels, tents, tarps and auto covers.

11. The process of claim 1 wherein said biologically active metal salt comprises a metal salt of silver, copper, zinc, cadmium, mercury, antimony, gold, aluminum, platinum, palladium, or combinations thereof.

12. The process of claim 1 wherein said cationic material comprises a material having a charge density greater than about 1 charged atom per about every 10 Angstroms of molecular length of said material.

13. The process of claim 1 said colloidal metal precipitate is physically trapped within a matrix of said cationic material.

14. The process of claim 1 wherein said colloidal metal precipitate is bound to said cationic material.

15. The process of claim 14 wherein adsorption binds said colloidal metal precipitate to said cationic material.

16. The process of claim 14 wherein electrostatic forces bind said colloidal metal precipitate to said cationic material.

17. The process of claim 1 wherein said microbiological interception enhancing agent comprising of a homopolymer of diallyl dimethyl ammonium halide wherein the halide is a counter ion of the ammonium cation, in combination with a silver salt, wherein the halide counter ion preferentially precipitates with at least a portion of the silver cation such that precipitation of the silver cation and the halide counter ion occurs in proximity to the homopolymer of diallyl dimethyl ammonium halide.

18. The process of claim 1 wherein said microbiological interception enhancing agent is stable on said dry article.

19. The process of claim 1 wherein said microbiological interception enhancing agent is stable on said dry article.

20. The process of claim 1 wherein said microbiological interception enhancing agent resides on said dry article.

21. The process of claim 1 further including drying said starting materials treated with said microbiological interception enhancing agent prior to fabricating said dry article.

22. A process of making an anti-microbial structure comprising:
   providing a plurality of nanofibers that are initially dry;
   providing a microbiological interception enhancing agent comprising a cationic material having one or more counter ions associated therewith and a biologically active metal salt;

treating at least a portion of a surface of at least some of said nanofibers with said cationic material to imparting a charge on said nanofibers;

rinsing said treated nanofibers with a substantially ion-free water to cause said counter-ions associated with said cationic material to be drawn tightly against said treated nanofiber surfaces and avoid unwanted ions that may cause uncontrolled precipitation of said biologically active metal into sites remote from the cationic surface;

exposing said rinsed, treated nanofibers to said biologically active metal salt, whereby said one or more counter ions of said cationic material preferentially precipitate with at least a portion of said biologically active metal salt such that precipitation of a colloidal metal precipitate occurs in direct proximity to said cationic material, while avoiding uncontrolled precipitation of said biologically active metal salt at sites of said nanofibers remote from said cationic material, such that, said microbiological interception enhancing agent resides on said at least portion of said surface of said nanofibers; and fabricating a dry article using said nanofibers having said microbiological interception enhancing agent whereby both said nanofibers and said microbiological interception enhancing agent reside throughout an entire thickness of the finished dry article.

* * * * *